United States Patent
Heath et al.

(10) Patent No.: US 7,573,034 B2
(45) Date of Patent: Aug. 11, 2009

(54) MOBILE RADIOGRAPHY IMAGE RECORDING SYSTEM

(75) Inventors: Michael D. Heath, Rochester, NY (US); Joshua M. Sibermann, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 5 days.

(21) Appl. No.: 11/436,311

(22) Filed: May 18, 2006

(65) Prior Publication Data

US 2006/0261296 A1    Nov. 23, 2006

Related U.S. Application Data

(60) Provisional application No. 60/682,362, filed on May 18, 2005.

(51) Int. Cl.
*G01T 1/10*      (2006.01)
*G01T 1/161*    (2006.01)
*G03B 42/04*   (2006.01)

(52) U.S. Cl. .............................. 250/361 R; 250/363.02; 250/370.08; 250/370.09; 378/181

(58) Field of Classification Search .............. 250/484.4, 250/370.08, 370.09, 589, 591, 361 R–363.02; 378/102, 181
See application file for complete search history.

(56) References Cited

U.S. PATENT DOCUMENTS

| | | | |
|---|---|---|---|
| 4,498,005 A * | 2/1985 | Oono et al. ............. | 250/484.4 |
| 4,960,994 A | 10/1990 | Muller et al. | |
| 5,081,357 A * | 1/1992 | Agano ...................... | 250/589 |
| 5,418,355 A | 5/1995 | Weil | |
| 6,069,935 A | 5/2000 | Schick et al. | |
| 6,553,094 B1 * | 4/2003 | Bernardi et al. ............... | 378/57 |
| 6,806,473 B2 * | 10/2004 | Honda et al. ........... | 250/370.11 |
| 6,850,597 B2 * | 2/2005 | Matsumoto et al. ......... | 378/154 |
| 6,855,936 B2 * | 2/2005 | Yamamoto ............. | 250/370.09 |
| 7,016,467 B2 * | 3/2006 | Brooks ....................... | 378/102 |
| 7,103,140 B2 * | 9/2006 | Amitani et al. ............... | 378/37 |
| 2004/0066899 A1 * | 4/2004 | Araki et al. ................. | 378/102 |
| 2005/0247898 A1 * | 11/2005 | Yonekawa .................. | 250/589 |
| 2006/0067474 A1 * | 3/2006 | Schmitt ...................... | 378/102 |
| 2006/0109958 A1 * | 5/2006 | Ertel et al. .................. | 378/205 |

\* cited by examiner

*Primary Examiner*—David P Porta
*Assistant Examiner*—Casey Bryant

(57) ABSTRACT

An apparatus for capturing information associated with an x-ray image recordable on an x-ray imaging plate. The apparatus is configured to be held in a hand of a user of the apparatus and includes a receiving area, a display, a replaceable rechargeable power supply, one or more non-image sensors, and a computer system. The receiving area receives the x-ray image plate or attaches the apparatus to the x-ray imaging plate. The non-image sensors collect information associated with the x-ray image recorded on the x-ray imaging plate. The computer system includes memory, and is configured to receive, measure, store, and subsequently communicate to another computer system, the collected information associated with the x-ray image recorded on the x-ray imaging plate.

21 Claims, 10 Drawing Sheets

MOBILE RADIOGRAPHY IMAGE RECORDING SYSTEM

CROSS REFERENCE TO RELATED APPLICATIONS

Priority is claimed from commonly assigned U.S. Provisional Patent Application No. 60/682,362 entitled "MOBILE RADIOGRAPHY IMAGE RECORDING SYSTEM", filed on May 18, 2005 in the name of Heath, incorporated herein by reference.

FIELD OF THE INVENTION

This present invention relates to an apparatus for the capture of radiographic images and metadata associated with radiographic images. More particularly, the present invention relates to an apparatus for the mobile capture of such images.

BACKGROUND OF THE INVENTION

Radiography refers to a general system, or modality, for recording a radiation image from the transmission of X-rays through the body of a patient. Conventional radiography uses a film/screen combination as a capture device while digital radiography can use either a flat-panel detector (DR) or stimulable phosphor plate (CR).

Radiographic examinations are common in health-care institutions, such as hospitals or tertiary care facilities. In some situations patients are transported into special examination rooms equipped for radiography while in other situations mobile radiographic equipment is transported to the location of the patient to obtain radiographs.

Mobile radiographic equipment provides a means to capture X-Ray images of objects using a transportable system generating and projecting an X-Ray beam through an object. Some implementations include only a means for generating an X-ray beam to expose an X-ray image recording plate, whereas other systems may additionally contain a means to retrieve an image from a plate. In general, these systems may be referred to as mobile or portable X-Ray exposure and/or capture systems. It is noted that other references to these systems use terms such as portable or mobile X-Ray generators. It is intended that similar reference refers to these types of systems.

In radiography, information that accompanies an image can be useful. For example, most images are typically stored with the name of a patient, the patient's medical record identification number, the time and date of capture, the body part, the x-ray projection and an identifier to indicate the radiographic technologist that acquired the image. Many types of additional information may also accompany an image such as, but not limited to, the exposure conditions of the radiograph, what type of scatter reducing grid was used, the patient position, the x-ray equipment used or the distance from the x-ray source to the patient.

In the typical practice of mobile radiography, minimal information is recorded with a radiographic image. The radiographic technologists that acquire the images may take notes of this information, or memorize it as x-ray exams are taken, then the information is manually input into a computer system at a later time. This information may subsequently be stored in a database or electronically with digital image data. One common representation for storing this information with an image in a medical facility is to represent the image and the data in a form supported by the DICOM standard.

Devices have been employed to assist in the collection of information relating to the acquisition of an x-ray image. U.S. Pat. No. 5,418,355 (Weil), commonly assigned and incorporated by reference, describes a system for manually collecting information relating to exam techniques using preprinted barcode charts and portable bar-code reader.

U.S. Pat. No. 4,960,994 (Muller) relates to management information pertaining to radiographic images, describing a cassette system with a rigidly attached memory for storing information related to an x-ray examination within a cassette.

SUMMARY OF THE INVENTION

An object of the present invention is to provide an apparatus to aid in the collection of mobile radiographic images with associated metadata. In one arrangement, the present invention provides a means to electronically record patient, exam, equipment, and technique information associated with the capture/recording of a radiographic image.

The present invention can provide a mechanism/means for electronically recording radiographic technique, equipment, and other information associated with a radiographic examination in the temporal or spatial setting of the examination to improve workflow for radiographic image capture and to minimize the likelihood of errors or emissions of data that may accompany entry of such data if not undertaken in temporal association with the examination.

The present invention can provide a means to electronically communicate data from the device to another computer system such that information recorded in association with the examination can be recorded in an electronic format with a digital representation of the radiographic image to which the information relates.

Further, the present invention can provide a means to receive, store, create, display, select, edit and communicate electronic records associated with medical image requests and other information obtained during radiographic examinations.

The present invention has a form factor/shape that allows it to be in contact with, and affixed to, interchangeable x-ray image receptors that, when attached, can be positioned by a radiographic technologist for capturing mobile radiographic images. Such a form factor allows sensors to automatically record information associated with the examination such as the use of scatter reducing grids or the orientation of an image receptor during an examination.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention, there is provided an apparatus for capturing information associated with an x-ray image recordable on an x-ray imaging plate. The apparatus includes a receiving area, a display, a replaceable rechargeable power supply, one or more non-image sensors, and a computer system. The receiving area receives the x-ray image plate or attaches the apparatus to the x-ray imaging plate. The non-image sensors collect information associated with the x-ray image recorded on the x-ray imaging plate. The computer system includes memory, and is configured to receive, measure, store, and subsequently communicate to another computer system, the collected information associated with the x-ray image recorded on the x-ray imaging plate.

According to another aspect of the present invention, there is provided a hand-held apparatus for capturing information associated with an x-ray image recordable on an x-ray imaging plate including a receiving area, a display, one or more non-image sensors, means for collecting data information, and a computer system. The receiving area receives the x-ray imaging plate or attaches the apparatus to the x-ray imaging plate. The non-image sensors collect information associated with the x-ray image recorded on the x-ray imaging plate. The apparatus includes means for collecting sensor data information from the one or more non-image sensors, and means for collecting non-sensor data information from a device in electronic communication with the apparatus. The computer system includes memory, and is adapted to receive and store the non-sensor collected data information and the sensor collected data information.

BRIEF DESCRIPTION OF THE DRAWINGS

The foregoing and other objects, features, and advantages of the invention will be apparent from the following more particular description of the preferred embodiments of the invention, as illustrated in the accompanying drawings.

DETAILED DESCRIPTION OF THE PREFERRED EMBODIMENTS

Figure 1:
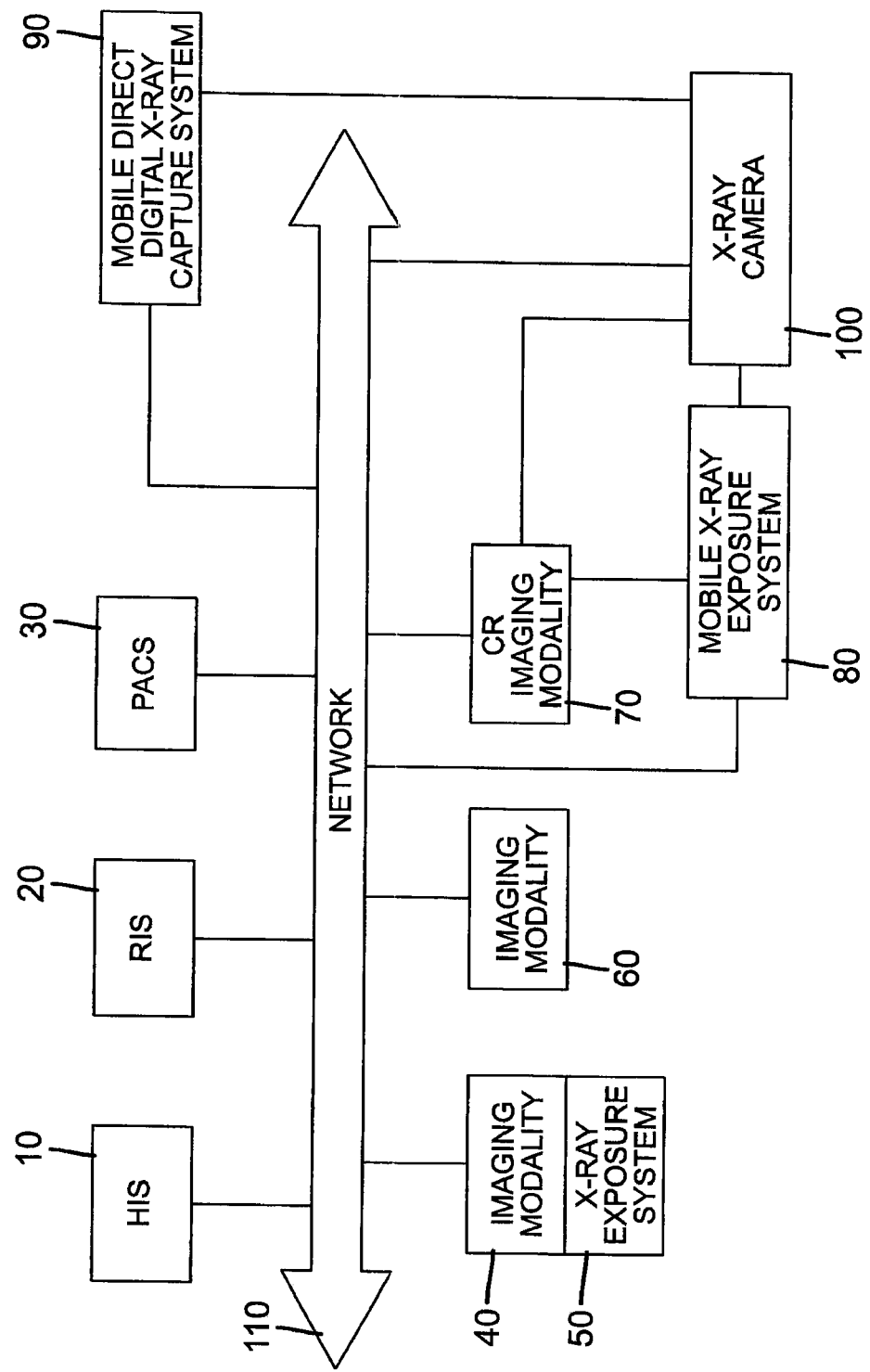
FIG. 1 illustrates an exemplary networked system comprising medical imaging systems, information systems, and picture archiving and communications systems (PACS), one or more mobile radiographic systems, and an x-ray image capture device/camera.

The following is a detailed description of the preferred embodiments of the invention, reference being made to the drawings in which the same reference numerals identify the same elements of structure in each of the several figures.

The present invention is now described with reference to FIGS. 1-6.

Figure 3A:
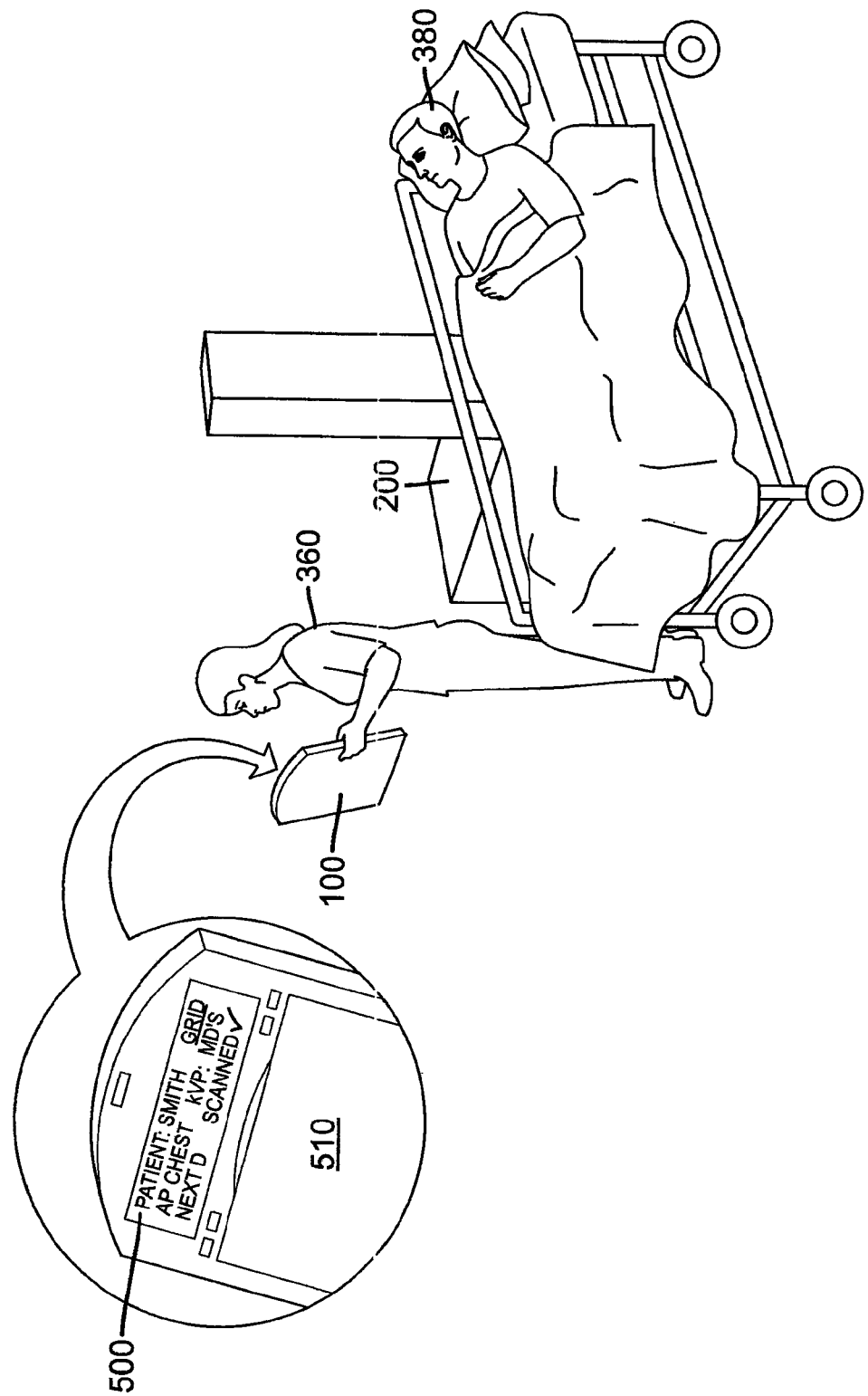
FIGS. 3A-3C diagrammatically illustrate one embodiment of the present invention, showing a hand-held apparatus with a cavity or receiving area that supports an x-ray imaging plate, and includes a touch screen computer display and a means to attach a scatter reducing grid.
Figure 3B:
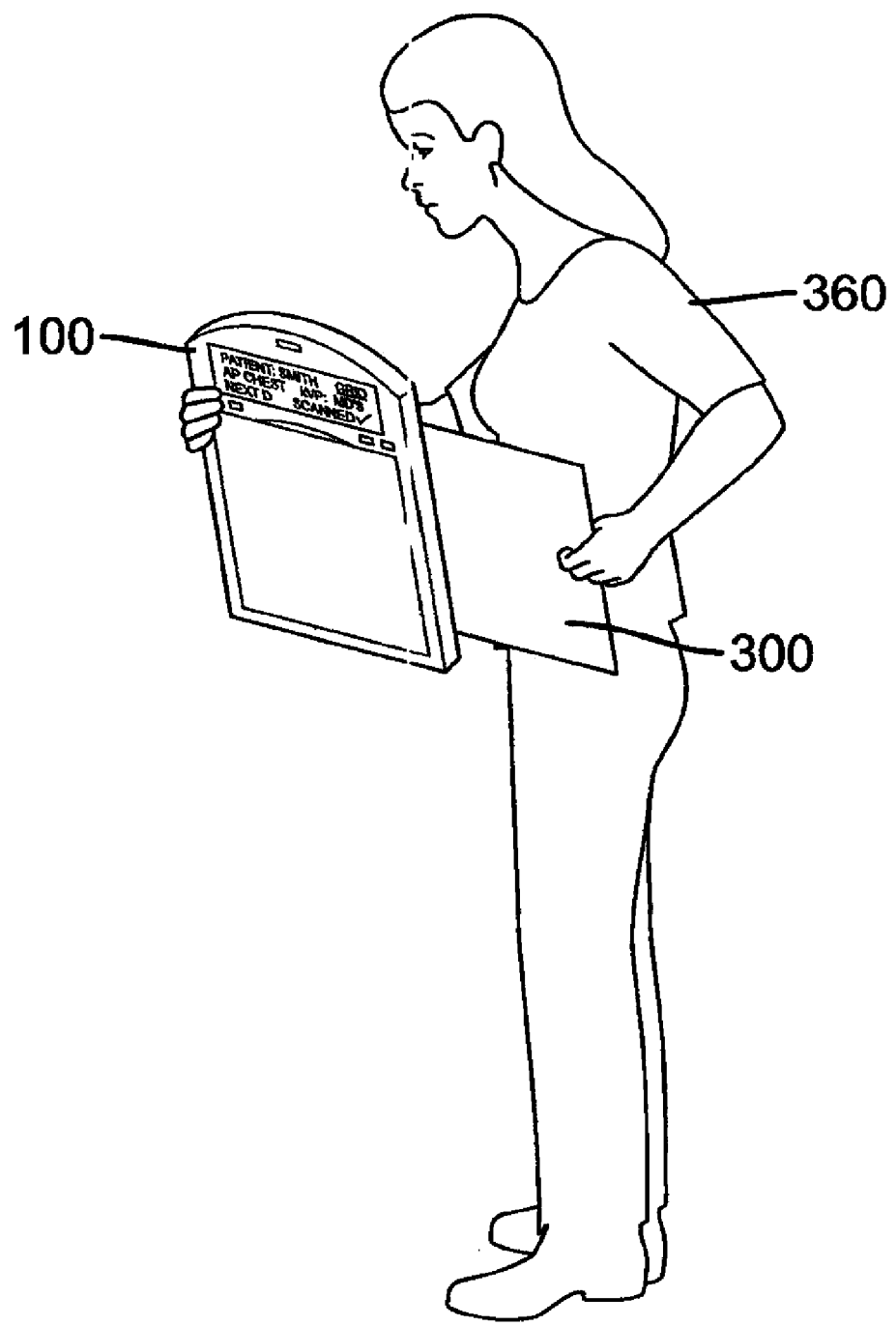
Figure 3C:
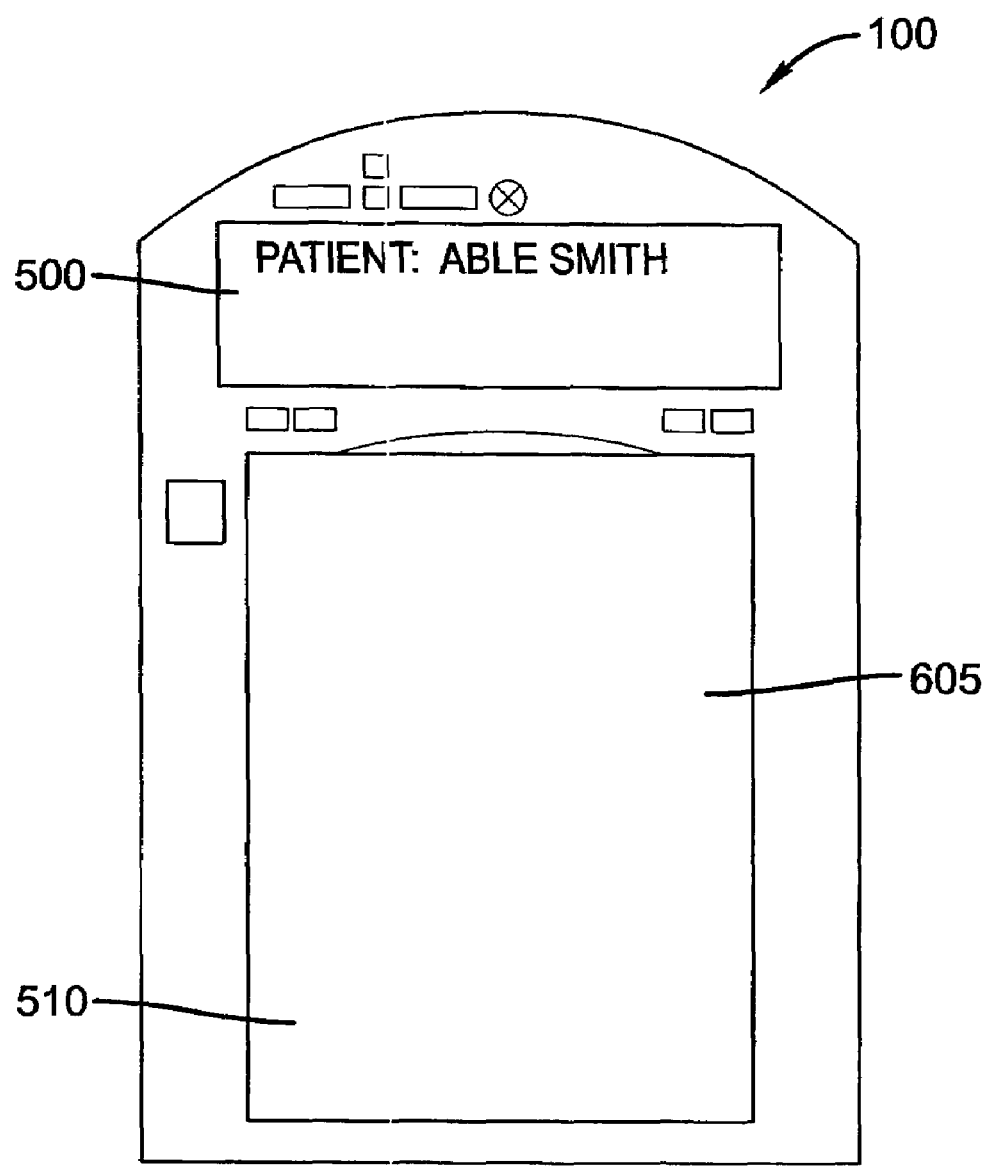

FIGS. 3A-3C show an embodiment of the present invention of an apparatus 100 that can be held in a hand of an individual during use of the apparatus. More particularly, the embodiment is an electronic apparatus 100 that can be held in a hand of a user and that enhances the procedures associated with the acquisition of radiographs with a mobile radiography system. This apparatus will be referred to as an x-ray information device or an X-Ray camera. Apparatus 100 is an element of a system of related devices, referred to as a mobile radiography image recording system, that function together to enable enhanced capabilities for portable radiographic imaging.

Apparatus 100 comprises a (built in) personal data assistant (PDA) computer that provides a computer processor system with a battery, a display 500, a user interface, computer memory, wireless electronic communications and one or more self contained non-image sensors. As shown in FIGS. 3A-3C, the apparatus, includes a housing configured to be held in a hand of a user of the apparatus, the housing being formed in a shape with a receiving area or cavity 510 capable of receiving an interchangeable radiographic imaging plate 605. The imaging plate may comprise a computed radiography cassette or a digital radiography image receptor. Use of a PDA is one means to implement several features of the present invention. These features may be implemented in alternative forms by integrating components rather than through the utilization of a pre-integrated PDA device.

The embedded computer system provides a user interface that is programmed to allow a radiographic technologist to create, recall, edit, and store computer records to aid in the capture and recording of information during the process of collecting images with a mobile radiography system.

A database in the computer system receives and stores medical image requests. Records of such requests can be displayed, sorted, and selected by the radiographic technologist. A user interface, shown on display 500, allows additional medical image requests to be entered into the device. New or recalled medical image requests can be selected to identify an electronic record of interest.

Apparatus 100 can include a bar code scanner which is electronically connected to the computer system. This scanner allows a radiographic technologist to use a bar code to input information and store it in association with a medical image request. In one embodiment of the invention, this bar code scanner is used to input a code to identify a computer radiography image receptor cassette used to acquire a radiographic image to satisfy the medical image request. Alternatively, a radio frequency ID (i.e., an RFID) system can be employed, such RFID systems being well known to those skilled in the art.

Cavity 510 (or another cavity) in the apparatus can accept the optional insertion of a scatter reducing grid 300. An electronic sensor embedded in the apparatus can be connected to the PDA to detect the presence or lack of a grid through electronic contacts with metallic contacts on the grid. The sensor can be adapted to identify individual grids by the layout of the electrical contacts on the grid. The connected PDA can then record an identifier for the grid if one is attached or the absence of a grid if one is not attached.

Additional sensors are also located in the cassette, including three tilt sensors embedded in three orthogonal directions. The sensors are connected to the PDA to allow the PDA to record the output of the three sensors to record the orientation of the apparatus relative to gravity while the device is in the position and orientation used to capture the radiographic image.

A wireless interface (such as BlueTooth or other well known wireless communication interfaces) can be employed to receive and record distance measurement data indicating the distance from the radiographic x-ray source to the patient (SPD) that is transmitted from, for example, a blue-tooth enabled laser distance sensor attached to the x-ray source.

Apparatus 100 can include touch screen display 500, physical buttons, or other operational members that allow a user to operate the apparatus in a range of modes.

Figure 6:
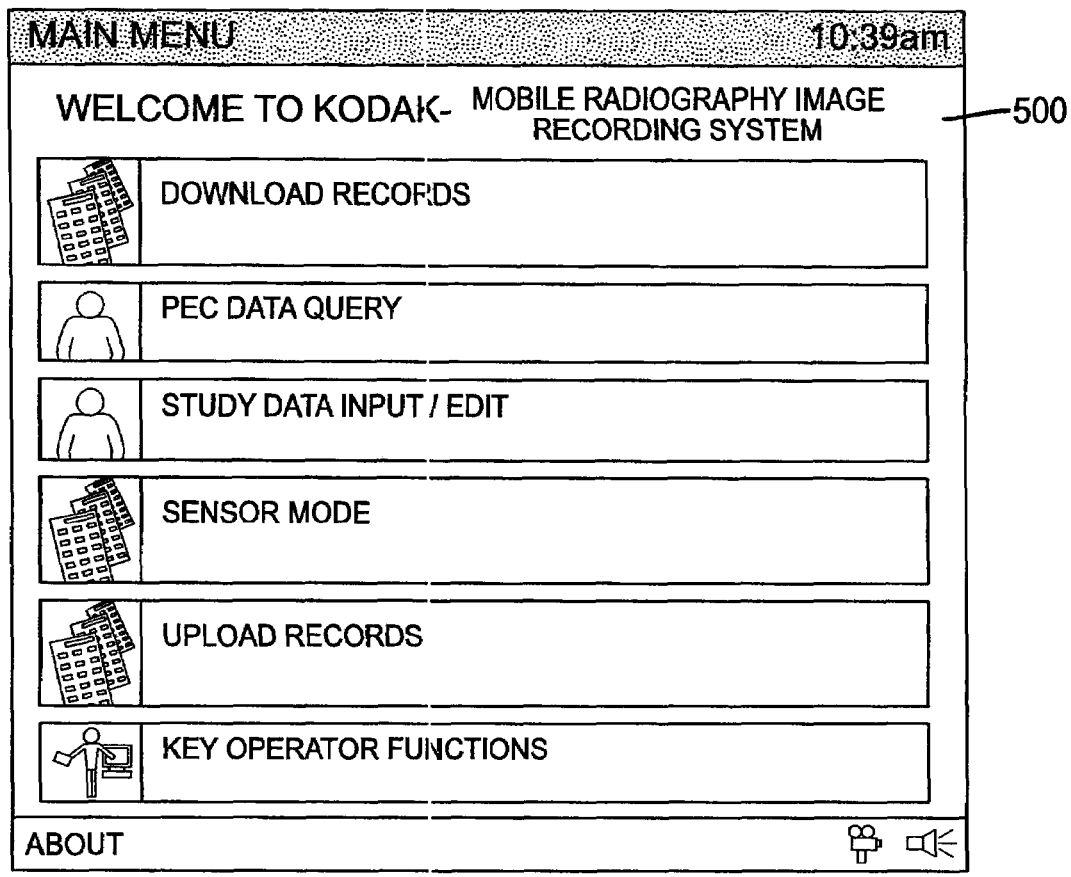
FIG. 6 shows examples of modes of operation of the apparatus of the present invention.

FIG. 6 illustrates possible modes of operation that can be selectable/viewed/accessible from display 500 by the user. For example, one mode allows the device to receive records from external information systems including both radiological information systems and computed radiography devices. Another mode allows the device to transmit data to external information systems such as, but not limited to, a radiological information system and a computed radiography plate reader device. Yet another operating mode allows the selection, display, edit capability and data recording and storage of medical records associated with the capture of a radiographic image. Further modes of operation are described below.

Figure 4A:
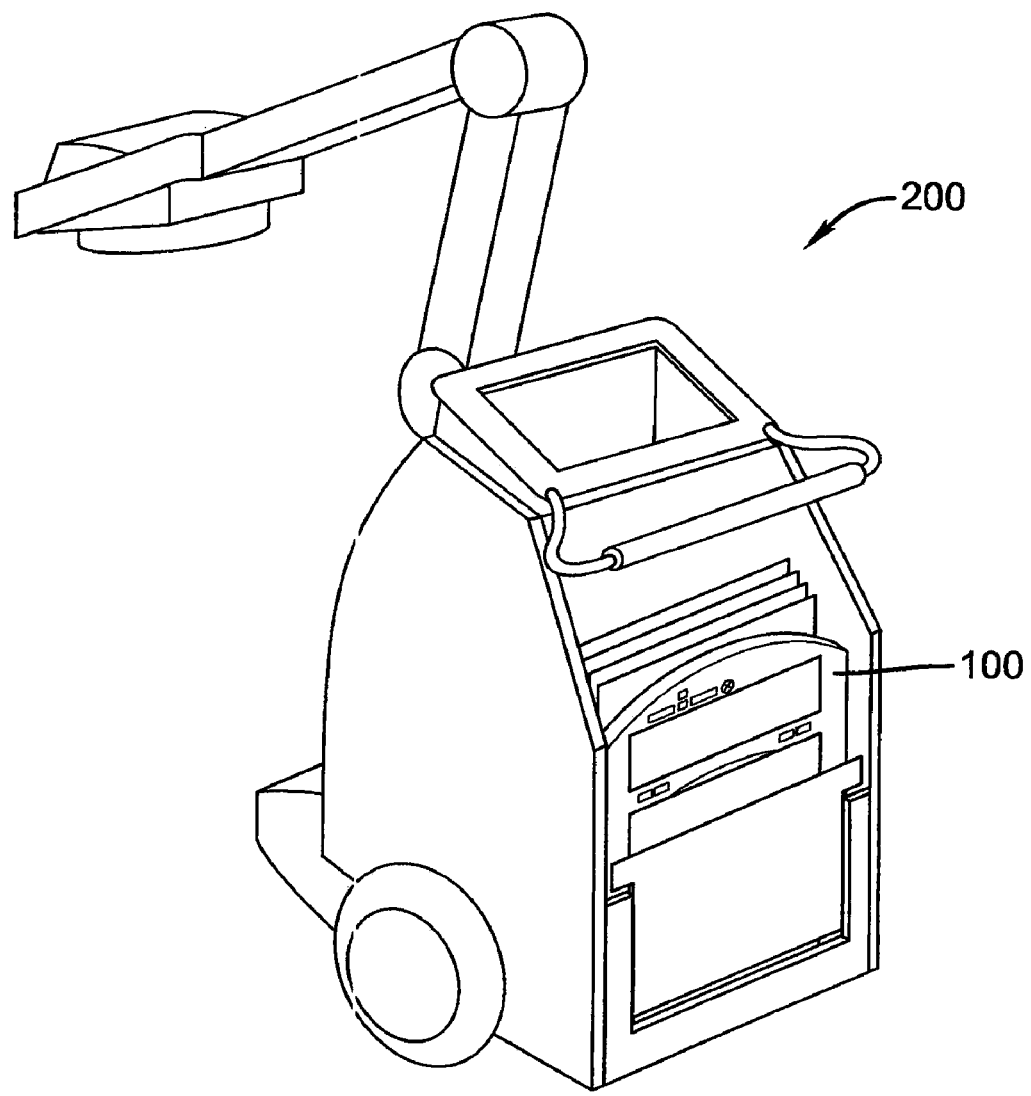
FIGS. 4A-4C illustrate the apparatus of the present invention employed for mobile transport to be used in association with the capture of a mobile radiographic image.
Figure 4B:
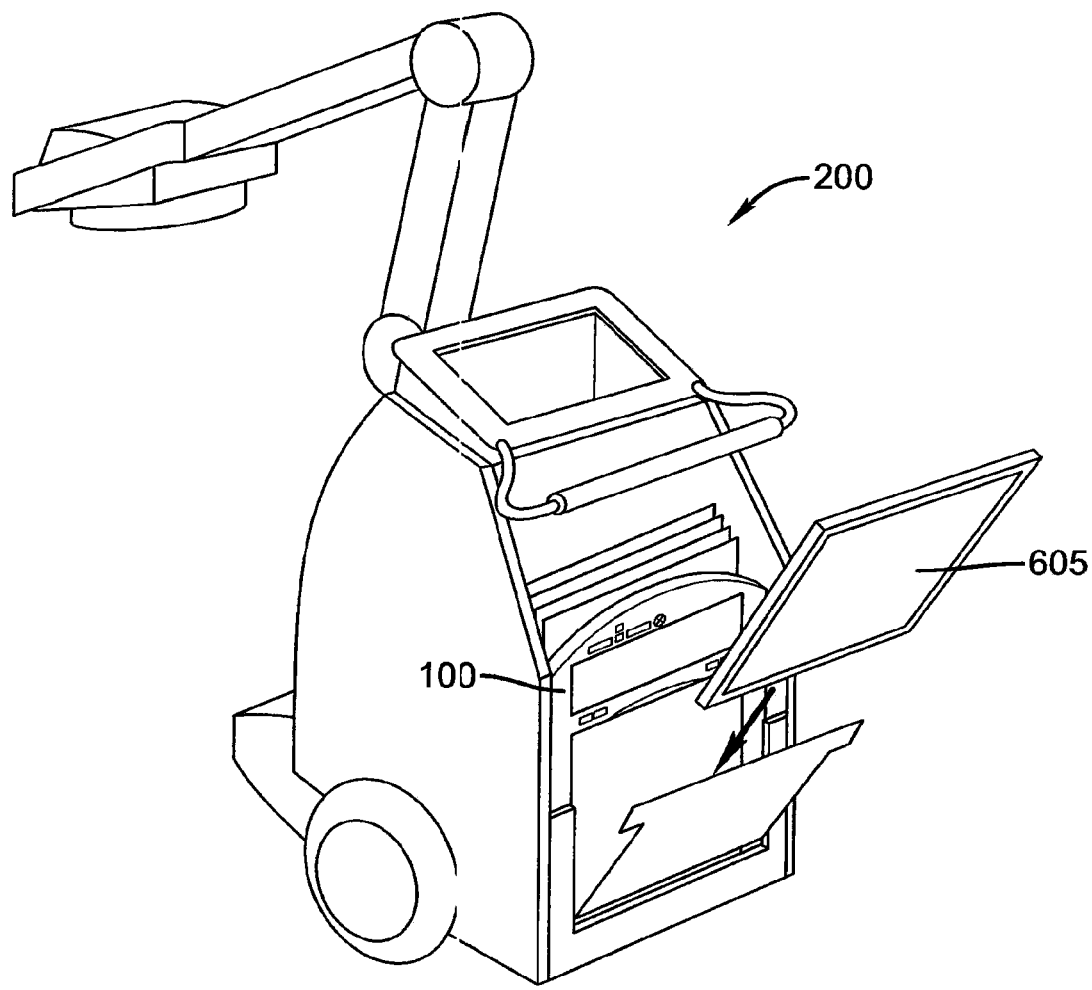
Figure 4C:
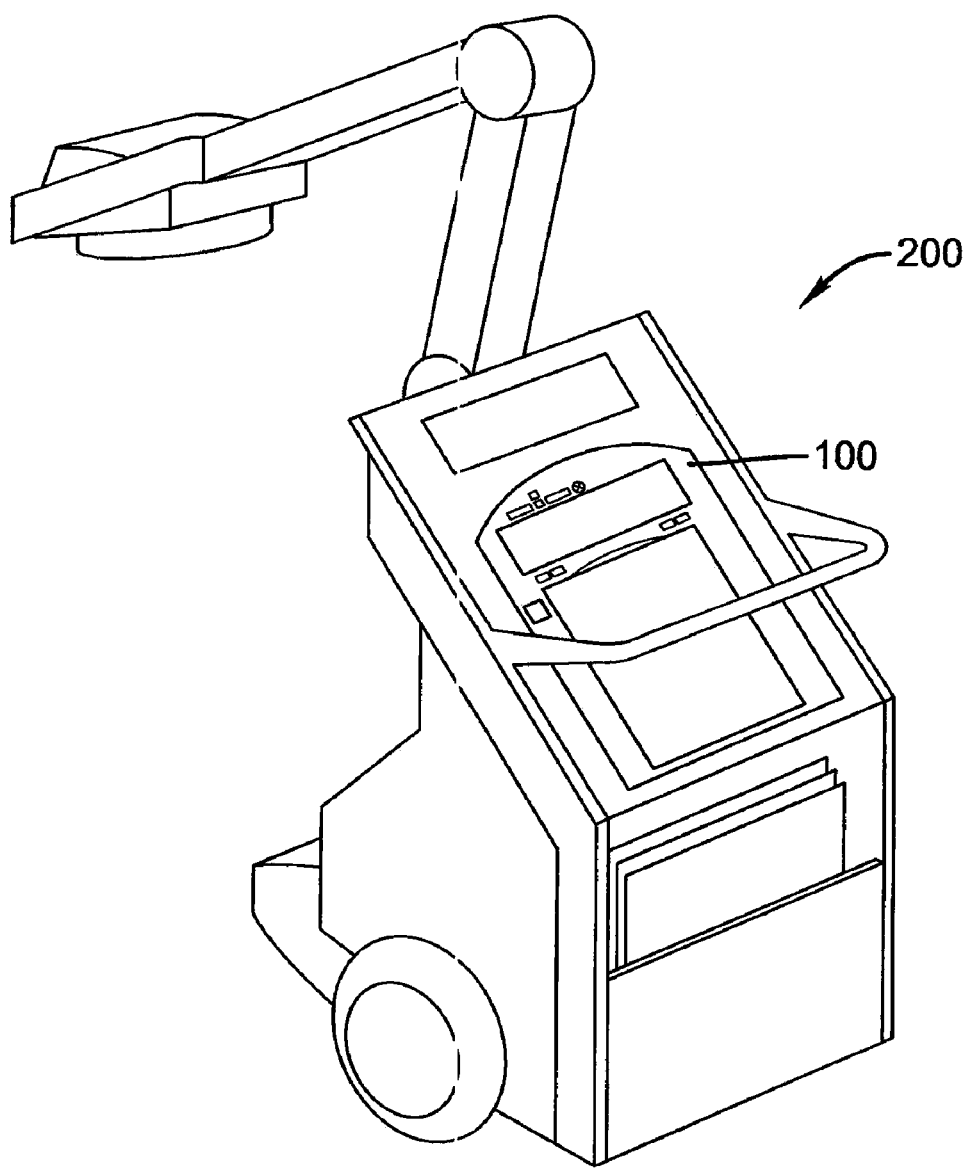

FIGS. 4A-4C illustrates how the form factor/shape of apparatus 100 allows it to be employed by a radiographic technologist for capturing mobile radiographic images.

Accordingly, an embodiment of the present invention is directed to apparatus 100 for capturing x-ray images of an object wherein apparatus 100 comprises cavity 510 for receiving or other means to attach apparatus 100 to an interchangeable x-ray image plate/receptor/cassette. Apparatus 100 further includes a replaceable and/or rechargeable power supply power supply 680, an electrical system, a computer processor 600, one or more non-image sensors and a computer memory that function to measure, store and subsequently communicate to another computer system, information associated with an image that is recorded by the interchangeable x-ray image plate that is attached to the apparatus.

Cavity 510 can be adapted to receive scatter reducing grid 300. A sensor can be employed to detect when a scatter reducing grid is attached to the apparatus, wherein the apparatus can record the presence or absence of the scatter reducing grid. A sensor can be employed to identify an individual grid where the identifier is associated with physical properties of the scatter reducing grid wherein the apparatus can record the identifier for the scatter reducing grid.

The function and modes of operation of the invention are now more particularly described.

FIG. 1 shows apparatus 100, which is an x-ray information device or x-ray camera, in association with other devices that function alone, or in concert, to capture, label, store, display, edit, transmit, archive and recall medical images.

A communications network 110 provides a backbone of medical imaging systems and connects multiple computer systems, and image acquisition, processing and display systems together. A hospital information system (HIS) 10 provides for the input, storage, manipulation and retrieval of information relating to patients. A radiological information system (RIS) 20 is another information system that is specialized to the management information associated with the acquisition of medical images. A picture archiving and communications system (PACS) 30 is a centralized or distributed computer system that functions to manage, store, retrieve and display medical images. Various medical imaging systems (for example computed tomography (CT), magnetic resonance imaging (MRI), positron emission tomography (PET), direct digital radiography (DR) and computed radiography (CR)) can be connected to network 110 to provide a means to acquire various types of medical images.

Medical imaging modalities (e.g. CT, MRI, PET, and the like) are represented at 60 in FIG. 1 on network 110. A plurality of imaging modalities of different types may be connected to network 110 at any given time.

Some imaging modalities 40, such as a direct digital mammography image capture system, provide a means to record a digital image of a subject that is exposed to an X-Ray beam, and are also directly connected to and integrated with an X-Ray exposure system 50 that includes an X-Ray beam generation means. Such a coupling in an integrated system allows for the setting and recording of X-Ray exposure techniques and conditions associated with the capture of a radiographic image.

A computed radiography imaging modality 70 reads latent images from exposed computed radiography cassettes. The exposure of the cassettes generally occurs using a separate X-Ray source such as a mobile X-Ray exposure system 80 that may not be integrated with or even connected to the computed radiography imaging modality 70.

X-Ray images may also be acquired by mobile direct digital radiography systems 90 that include both X-Ray generator systems and direct digital X-Ray image recording devices.

In the capture of mobile radiographic images, the image receptor or a cassette that houses the image receptor is not typically connected by a mechanical means to the X-Ray exposure/capture system. The receptor may either have no physical connection, or may have an electrical connection to the X-Ray mobile X-Ray system. The receptor is not placed in a buckey system that is part of the overall X-Ray imaging system.

X-Ray camera 100 is used in the capture of mobile radiographic images. X-Ray camera 100 provides a functional means to record sensor measurements associated with the planning for, or capture of, an X-Ray image. X-Ray camera 100 also provides a means to communicate directly with mobile X-Ray exposure 80 or mobile direct digital capture systems 90 with on-board computer systems or a CR imaging modality 70 and a means to communicate with a computer network. Communication with network 110, in turn, provides a means to communicate with other information systems such as, but not limited to a HIS 10 or a RIS 20 system.

Figure 2:
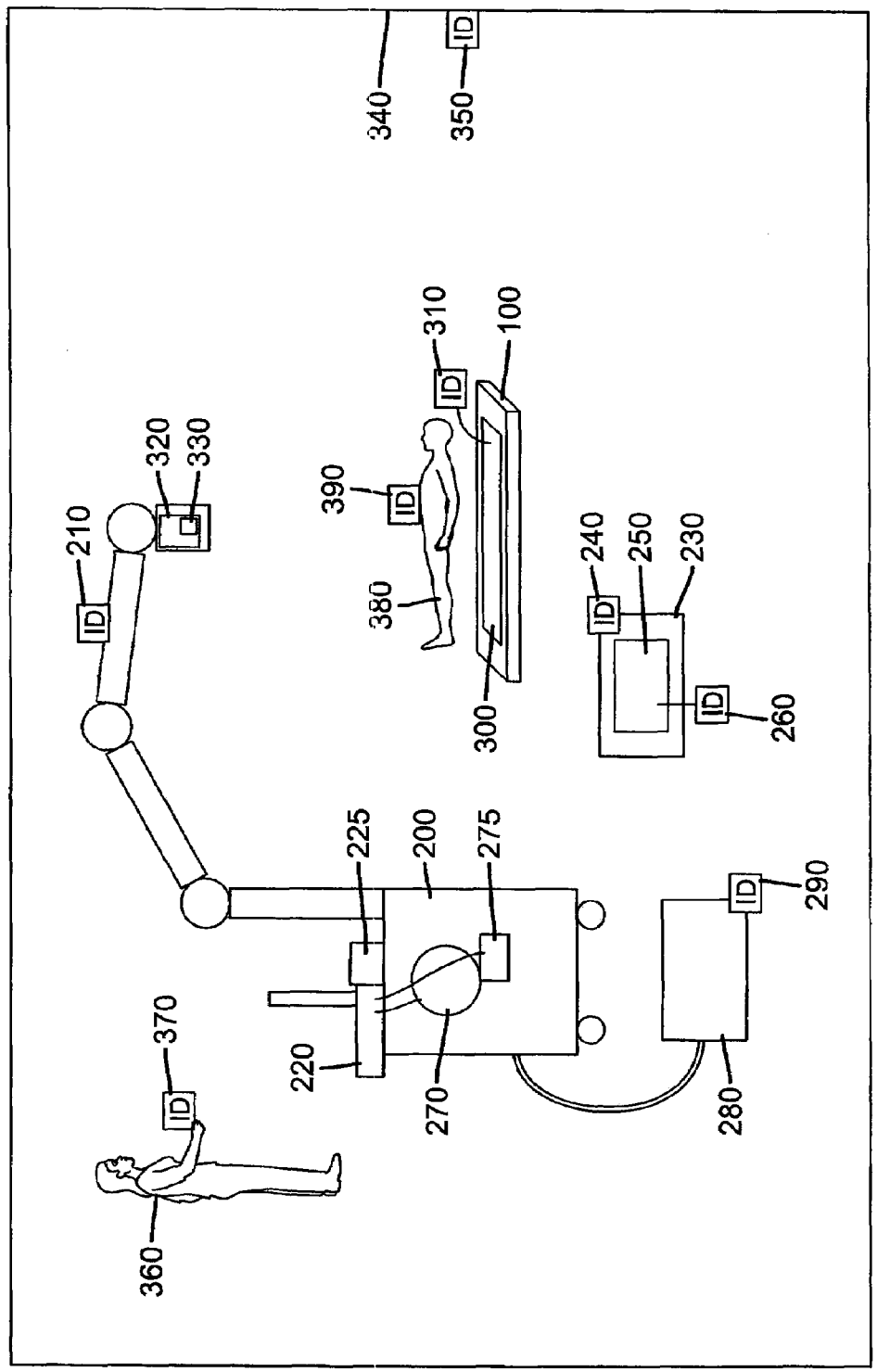
FIG. 2 shows an exemplary mobile x-ray system for imaging a patient with a plurality of equipment that can be associated with the capture of radiographic images.

FIG. 2 illustrates X-Ray camera 100 in an arrangement for acquiring portable radiographic images. A portable X-ray capture system 200 is used to generate an X-Ray beam that passes through patient 380 and expose an image plate/receptor/cassette associated with X-Ray camera 100. Portable X-Ray capture system 200 refers to either a mobile direct digital capture system 90 or a general purpose mobile X-ray exposure system 80 for the capture of images with imaging cassettes containing either computed radiography image receptors or film screen cassettes.

In the arrangement where portable X-Ray capture system 200 is a direct digital capture system, imaging plate 605 will be a direct digital X-Ray image receptor 280 and a computer system 220 enables the capture and/or image processing of images with the receptor.

In the arrangement where portable X-Ray capture system 200 records images with a computed radiography cassette 250, the cassette includes a CR phosphor storage sheet 260 as the image receptor/imaging plate. Some portable radiography capture systems may also include an integrated computed radiography reader device 270 and an on-board computer system 220 that collectively function as a mobile computed radiography imaging modality 70.

With portable x-ray capture system 200, the capture of portable radiographic images employs, patient 380, a X-Ray generator source of portable capture system 200, a technologist 360 operating the equipment, and imaging plate/receptor 605.

In addition to these components, additional components may be used to aid in the capture of portable radiographic images. For example, scatter reducing grid 300 can be used to reduce the amount of scattered radiation in an image. In a preferred embodiment of the present invention, X-Ray camera 100 can employ multiple scatter reducing grids with different physical properties.

A distance sensing device 320 may be used to measure a distance from the X-Ray source focal spot to the patient for the exam. The distance sensing device employs a communication means, such as a wireless communication system 330, that allows the device to receive a request to make a distance measurement. The device determines the distance measurement, and the communication means can communicate the distance measurement to another device. In an embodiment of the present invention, this communication occurs wirelessly across a BlueTooth wireless connection. Multiple technologies may be used to implement distance measurements and example technologies include but are not limited to infrared sensors, ultrasonic distance sensors and laser rangefinders. The preferred embodiment of the present invention uses a laser distance measuring technology.

With the array of devices that can be employed to capture a specific radiograph, a feature of the present invention offers a means to automatically identify these devices and take measurements with these devices of the conditions associated with the planning for, or capture of such images.

Figure 5:
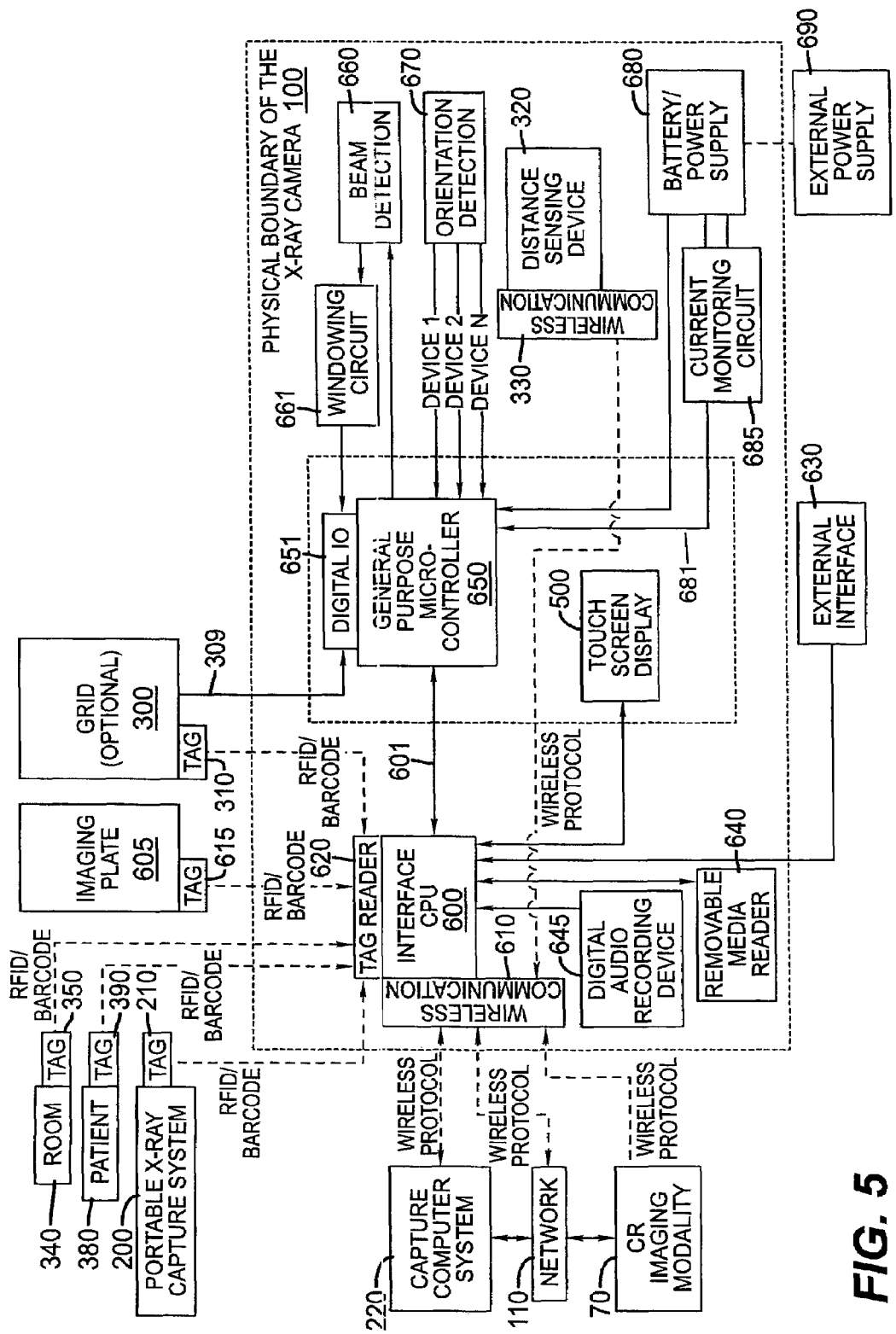
FIG. 5 shows exemplary subsystems and sensors which can be employed with the present invention.

Each device and/or individual can be associated with an identification tag/marker/device. For example, radiographic technologist 360, portable X-Ray capture system 200, patient 380, scatter reducing grid 310, DR image receptor 280, CR cassette 230, CR phosphor sheet 250, and/or room 340, may have identification tag 370, 210, 390, 310, 290, 240, 260, and 350 respectively, as shown in FIGS. 2 and 5.

The identification tag stores a code that relates to a description, and/or properties of a device or object. Identification tags preferably use some technology such as RFID or bar codes to allow other devices to automatically sense and record the coded identification. The preferred embodiment of the present invention uses RFID identification devices, though any technology that allows computer controlled recovery of the identification codes can be employed with the invention.

Referring to FIG. 3A, touch screen 500 can provide a display and user interface for controlling X-Ray camera 100 in a variety of modes. Information stored in the device may be displayed, manipulated, stored and recalled. FIG. 3A also shows cavity/receiving area 510 for holding imaging plate 605. FIG. 3B shows X-Ray technologist 360 attaching scatter reducing grid 300 to X-Ray camera 100.

FIGS. 4A-4C show illustrations of X-Ray camera 100 attached to portable X-Ray capture system 200. FIG. 4A shows a mounting system. FIG. 4B shows a mounting system that holds X-Ray camera 100 in a manner that allows image plate 605 to be inter-changed. Shown in FIG. 4C, mounting X-Ray camera 100 on portable radiography system 200 allows it to be transportable without a need for it to be carried. The mount may have a connection to the electrical system of the portable X-Ray capture system that also connects to the power supply in X-Ray camera 100 to recharge the power supply/battery 680.

FIG. 5 shows components in the X-Ray camera as well as references to external devices with which the X-Ray camera can interact.

An on-board computer 600 serves a role in the collection, association, storage and communication of data related to an X-Ray examination. For ease and clarity, the on-board computer will be described as a common personal data assistant computer, though it is recognized that the same functionality of the invention could be implemented from components in lieu of utilization of an off-the-shelf component such as a personal data assistant computer (PDA). Computer 600 is also referred to as an interface computer in the X-Ray camera.

The PDA includes a computing means, a power supply, and a memory providing the attributes of a general computer processor system. Additionally, the PDA includes touch screen display 500 for displaying data and allowing a user to interact with the device. Removable media reader 640 is included within the device to allow the storage and retrieval of data on a removable storage medium. Different types of memory devices may be used, such as, but not limited to Compact Flash cards, secure digital cards and memory sticks. The PDA also includes a digital audio recording system 645 that can be used to collect audible information such as a technologist's comments.

The PDA can further include one or more wireless communication systems 610, such as, but not limited to Blue-Tooth and Wi-Fi. This wireless communication means provides communication channels to communicate with a distance sensing device's 320 wireless communication system 330, with an external computer 220 associated with a portable X-Ray capture system 200 through a communications interface 270, to a computed radiography imaging modality 70 and to a medial computer network 110. Connection to this network 110 facilitates communication with other systems on the network, such as a HIS 10, a RIS 20 and a PACS 30. These network connections may be transitory based on need or availability at a particular time. Operations that are performed by the X-Ray camera that do not depend on a connection not associated with a particular function of the device may proceed without that connection.

PDAs include serial interfaces and expansion slots that allow expansion of their capabilities by connecting them to other devices. In FIG. 5, device 620 refers to one or more devices for inputting device identification data. This may be a bar-code reader, an RFID reader, another device or some combination of devices. Commercial, off-the-shelf, small, low power devices are available on the market, such as the Socket CF RFID card 6E (Product ID: RF5400-542) for reading RFID identification tags and the secure digital scan card 3E (Product ID: IS5300-464).

A general purpose microcontroller 650 is used to collect lower level sensor information. As shown in FIG. 5, the microcontroller can be connected to a variety of sensors either directly or through an established wireless protocol such as Bluetooth or Ultra-wide Band. These sensors can include (but are not limited) to x-ray beam detector 660, distance sensing device 320 that could be used for source-to-image distance (SID) measurement, an electrical contact sensor 309 for detecting the presence of scatter reducing grid 309, grid identification device 310, orientation detector 670, time of exposure, and duration of exposure. The microcontroller can be connected to interface CPU 600 via communications bus 601 that handles higher-level interfaces (wireless protocols, hospital works, and the like). The microcontroller will be idle in a deep-sleep, power-saving state or doing some sort of background processing until interrupted by a chosen external event. Once interrupted, the microcontroller will read each of the connected sensors in some predefined order and populate a data structure that at some later point may be passed to the interface CPU.

In one mode of operation, beam detection sensor 660 serves as a wake-up interrupt. Wireless imaging cassettes have been proposed that operate independently of the main system by using X-ray sensors in the imaging cassette to detect the onset and terminate of the impinging X-rays from the remote X-ray source. An example of a wireless and/or independent X-ray impingement sensing is described in U.S. Pat. No. 6,069,935. Dedicated X-ray event trigger diodes located in the imaging cassette outside the imaging panel can be monitored by a computer to detect incident radiation and output a signal indicating same. Upon receiving a trigger, sensors will be interrogated and their information stored, reflecting the parameters at the time of exposure with limited technologist intervention. The actual time of the trigger will be recorded as well for association with the data collected from other sensors.

A brief sensor summary follows.

The x-ray beam detection signal serves a plurality of purposes. In addition to serving as the system "start" signal, the signal will be windowed using some means of threshold detection 661 to determine beam duration. In one embodiment, an analog comparator set with an appropriate threshold to ignore any noise sources provides a start/stop signal to a digital counter synched to the x-ray beam coming on and off. Depending on the means of beam detection, the threshold scheme could either be passive (fixed) or active (real-time) adjustable to account for such environmental variables as ambient light which could move the mean signal level around. Additionally, in order to ensure that this sensor will receive x-ray flux regardless of how a beam might be collimated, multiple sensors may be used and placed such that the probability of x-ray reception is high.

Orientation detection of imaging plate 605 can be deduced from external devices measuring the gravity vector and some geometric transformations. More particularly, orientation detection of imaging plate 605 can be deduced from N discrete devices 670 measuring components of the gravity vector (i.e. accelerometers) and some simple geometric transformations where N depends on the tilt angles desired to be measured. In one embodiment, accelerometers in an orthogonal arrangement can be used to deduce the tilt angles of imaging plate 605. When queried by microcontroller 650, the accelerometers digitally transmit their information to the microcontroller over a serial interface (i.e. SPI, I2C) and the microcontroller calculates the tilt angles using known trigonometric formulas or a pre-populated LUT. Alternatively, the microcontroller could directly sample the accelerometer's voltage output with either an on-chip or off-chip Analog-to-Digital converter. More complete devices performing both of these functions, such as laser leveling devices used for construction and home improvement could also be used. Information could be transferred serially to the microcontroller or over BlueTooth or other wireless technology to the PDA CPU 600.

X-Ray camera 100 can be used selectively with a variety of individual means for recording an X-Ray image. In FIG. 5, the image recording means is referenced as imaging plate 605. This imaging plate may refer to computer radiography cassette 230 or direct digital radiography image receptor device 280, either of which can be placed in cavity or receiving area 510. An identification device 615 is a general reference to the identification device associated with imaging plate 605. This may be 230, 260 or 290 depending on the imaging plate used with the X-Ray camera.

For image post-processing purposes, the information of whether scatter reducing grid 300 was present in an exposure (and if so, its properties, for example, grid ratio, grid line frequency, lead thickness, and the like.)may be recorded. There are several methods to perform this identification using the defined system.

One method would be to place RFID tag 310 on the grid with the particular information encoded. The presence of a "grid tag" indicates that a grid was present for exposure and the information on the tag would possess a known structure such that the system could extract all necessary grid properties.

Alternatively, identification tag 310 could contain a code that is used to access the properties of that grid from a database that stores the grid properties and the grid identification code. The RFID reader would likely be attached to the PDA CPU.

Alternatively, a hardwired approach could be employed using the microcontroller. One method could involve placing small metallic contacts of various arrangements on the grid. The arrangements would be indicative of the grid specific properties or of a code that relates the grid identity to it's properties by consulting a database of grid information. When the grid was engaged in the holder, the contacts can be differentiate (for example, differential voltage, frequency, current, and the like). If some contacts are pulled to a high voltage while others are pulled to ground, these contacts could be read in through the microcontroller's digital IO port 651. Grid presence would be inferred and grid properties could be determined by the contact's arrangement.

Source-to-Patient (SPD) measurement can be performed by a remote device mounted to x-ray tube assembly 320. A plurality of off-the-shelf devices are able to accomplish this task using various known technologies including laser interferometry, ultrasound, or infrared signals. Consumer devices can obtain accuracies to within 1 cm. In a preferred embodiment, the SPD detection device 320 can be polled for data over a wireless communication channel 330, such as BlueTooth, to enable the device to operate from a position attached to the X-Ray head.

The communication channel between interface CPU 600 and microcontroller 650 could be a standard serial interfaces such as SPI, I2C, and the like. If an SPI bus, interface CPU 600 could be the master while the microcontroller would be one slave on the bus. This provides expandability in several ways. New components can be connected to interface CPU 600 or microcontroller 650 directly or new devices can be added to the serial bus independent of the microcontroller. Interface CPU 600 would need to control which slave device was active on the bus.

Battery operated power supply 680 can power the system. Performance targets include minimal weight and maximum battery lifetime. Battery lifetime is preferably at least one hospital shift. The prevalence of portable devices has driven battery technology such that lightweight battery packs are readily available. One such technology is lithium-polymer. Depending on the requirements, a battery pack can be created with multiple cells in series or parallel. The type of regulator (linear, switch mode, and the like) will be driven by spatial requirements and loading as well as battery lifetime targets.

Included in the power supply is means for the microcontroller to detect end-of-life. One such method would be a circuit 685 to monitor voltage and or current draw at the power supply to determine power supply capacity. Some known battery packs include integrated circuits that monitor the battery's state of charge to prevent unsafe use of the device. This device is available over a serial interface 681, often I2C. The microcontroller could maintain a complete battery understanding using this method.

Employing the above description of the X-Ray camera and the objects associated with the capture of radiographic images, the following descriptions of the methods of operation of the X-Ray camera assist to more particularly describe embodiments of the present invention.

Four system modes are described regarding obtaining non-sensor data using the system. More particularly, Mode 1 comprises downloading a work list from a network system; Mode 2 comprises downloading previous exposure information relating to a specific criterion (i.e. patient ID); Mode 3 comprises downloading missing information based on existing information in a work list; and Mode 4 comprises new study information being pushed into the local system work list from a network.

NON-SENSOR DATA MODE 1—Mode 1 comprises downloading a work list from a network system. Technologist connects mobile radiographic image recording system to network; system queries network for more radiographic requests (updated work list); system downloads work list onto interface CPU.

NON-SENSOR DATA MODE 2—Mode 2 comprises downloading previous exposure information relating to a specific criterion (i.e. patient ID). Technologist connects mobile radiographic image recording system to network; system queries network for previous exposures of patient(s) to be imaged; system download previous exposures to guide technologist on new exposure.

NON-SENSOR DATA MODE 3—Mode 3 comprises downloading missing information based on existing information in a work list. Technologist connects mobile radiographic image recording system to network; technologist recalls record with missing information (i.e. patient ID); system queries network for missing information given existing information in record (i.e. patient name); system downloads information and amends record.

NON-SENSOR DATA MODE 4—Mode 4 comprises new study information being pushed into the local system work list from a network. Network given a new radiographic request tied to specific technologist; network waits for given mobile radiographic image recording system to appear on network; when system appears network downloads additional study into work list; system alerts technologist of new request.

Three system modes are described regarding obtaining sensor data using the system. More particularly, Mode 1 is an automated mode where a suite of data is collected in a fully automated fashion; Mode 2 is a mode where specific data is requested from the local touch screen display (this could be used, for example, to augment an incomplete patient record); and Mode 3 is a mode where specific data is requested from a capture computer system that is connected to an x-ray generator (this could be used, for example, to request grid data and/or SPD information prior to configuring a generator for exposure).

SENSOR DATA MODE 1—Mode 1 is an automated mode where a suite of data is collected in a fully automated fashion. Imaging plate 605 is loaded into camera 100; mobile radiographic image recording system 200 put into Sensor Mode; camera is placed behind the patient; x-ray source is positioned; x-ray beam is fired; beam detection circuit 660 senses beam; microcontroller 650 records local sensor information; state of camera is set to "exposure sensed/not processed; polling interface CPU detects state of "exposure sensed/not processed; interface CPU sets its state to "exposure processing"; interface CPU retrieves data from microcontroller; interface CPU records local sensor information; interface CPU combines local data and microcontroller data into single data record; data record is stored in one or more types of memory; interface CPU sets its state to "exposure processed"; microcontroller senses CPU state of "exposure processed" and sets its state to "ready-for-exposure".

SENSOR DATA MODE 2—Mode 2 is a mode where specific data is requested from the local touch screen display. Technologist sets up radiographic study; mobile radiographic image recording system put into Device Specific Mode via touch screen display; technologist requests information from any sensor present in the system; appropriate processing unit collects data and passes it to the interface CPU; data from sensor is displayed for user; data is associated with any other information of the device as directed by the user.

SENSOR DATA MODE 3—Mode 3 is a mode where specific data is requested from a capture computer system that is connected to an x-ray generator. Technologist sets up radiographic study; mobile radiographic image recording system is remotely put into Device Specific Mode via capture computer system; capture computer system requests information from any sensor present in the system; appropriate processing unit collects data and passes it to the interface CPU; data from sensor is communicated back to the capture computer system; mobile radiographic image recording system is placed back into the mode it was in before it was placed in Device Specific Mode; capture computer system utilizes collected data; technologist may refine radiographic study setup based on sensor feedback.

Five system modes are described regarding how data stored on the mobile radiographic image recording system can be transferred out of the capture system. More particularly, Mode 1 is a direct connection to a capture computer system; Mode 2 is a direct connection to a walk-up CR reader; Mode 3 is an indirect connection using removable media; Mode 4 is a similar case to modes 1,2 and 3 except no matching record found; and Mode 5 is for a DR portable X-Ray capture system or a portable X-Ray capture system with an on-board CR plate reader device.

TRANSFER MODE 1—Mode 1 is a direct connection to a capture computer system. Upon completion of information collection with the device, technologist inserts CR cassette into mobile CR reader; mobile CR reader scans cassette ID in preparation to read; mobile reader queries data stored on interface CPU looking for a match; system download matching record and associates it with CR image being read.

TRANSFER MODE 2—Mode 2 is a direct connection to a walk-up CR reader. Identical to Mode 1 (described above) except that CR reader is a walk-up terminal that connects to interface CPU's wireless communication.

TRANSFER MODE 3—Mode 3 is an indirect connection using removable media. Information has been stored on removable media (flash drive, CF, and the like) by the mobile radiographic image recording system; technologist removes media; technologist caries exposed cassettes (without full system) to CR walk-up terminal; technologist inserts removable media into walk-up terminal; technologist scans exposed CR cassettes; terminal is pointed to find matching records on removable media.

TRANSFER MODE 4—Mode 4 is a similar case to Transfer Modes 1, 2 and 3 except that no matching record is found. In Transfer Modes 1, -3, the information collected by the mobile radiographic image recording system is automatically associated with additional information such as a patient record or X-Ray exam request/order. In this mode of operation, the X-Ray technologist manually recalls stored information or inputs new information and associates it with the data obtained from the mobile radiographic image recording system.

TRANSFER MODE 5—Mode 5 is for a DR portable X-Ray capture system or a portable X-Ray capture system with an on-board CR plate reader device. Post X-Ray image exposure, the capture computer system initiates a download of one or more data records from the mobile radiographic image recording system and associates it with the digital image of the object. After download, the data record is associated with the digital image that resulted from the exposure by associating either the time of X-Ray exposure or the identification of the imaging plate (in the case of CR).

The present invention provides some advantages. For example, the present invention provides an automated means for collecting exam specific information related to the capture of portable X-Ray images so the information is captured with minimal impact to the activities of radiographic technologists. In addition, the present invention provides a means to collect information related to an X-Ray exam capture before the X-Ray exposure takes place to collect information that can be used to set exposure conditions or techniques for the X-Ray image exposure. Still further, the present invention provides a means to store the collected exam specific data in a memory that is external to the imaging plates or cassettes used to record the image. As such, cost savings occur because the system does not require implementation of sensor, processor or storage means in each imaging receptor or cassette. The present invention further provides a communications means to allow other devices to upload and download data to this device as well as a means for the device to upload or download data from other devices. Exam requests, patient data, exam data or other information may be exchanged through these communications.

Particular attributes of the present invention include, but are not limited to: the automated collection of non-image information can be triggered by beam detection; the collection of information by request from a capture computer (i.e., the data collection can be accomplished without triggering an X-ray); the manual initiation of the capture of information; ability of information display and editing; the association of collected data to other information/records; ability to use with standard CR, CR on the portable X-Ray capture; sensors can be readily added to or removed from the system; digital audio can be collected and associated with other data collected by the system (for example, used to capture comments from a technologist); ability to upload worklists by various initiators of the transfer; acquired data can be communicated to multiple devices with communication initiated by multiple devices; and communication of data can occur in wireless mode or by use of removable media.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10 Hospital information system
20 Radiological Information System
30 Picture Archive and Communications System
40 Direct digital mammography system
50 X-Ray exposure system
60 Other imaging modality
70 Computer Radiography Imaging Modality
80 Mobile X-Ray exposure system
90 Mobile digital capture system
100 X-Ray camera or x-ray information device
110 Communications network
200 Portable X-Ray capture system
210 Portable X-Ray capture system identification device
220 Portable X-Ray capture system computer
225 Portable X-Ray capture system communications interface
230 Computed radiography cassette
240 Computed radiography cassette identification device
250 Computed radiography image receptor (phosphor sheet) or cassette
260 Computed radiography image receptor identification device
270 Computed radiography image receptor readers
275 CR plate ID reading device
280 Direct digital radiography image receptor
290 Direct digital radiography image receptor identification device
300 X-ray scatter reducing grid
309 Electrical contact based sensor for detecting a scatter reducing grid and its identity
310 X-Ray scatter reducing grid identification device
320 Distance sensing device
330 Wireless communication system
340 Room/current location of the x-ray system
350 Room identification device
360 X-Ray technologist
370 X-Ray technologist identification device
380 Patient or subject of X-ray imaging
390 Patient identification device
500 Touch screen computer display
510 Cavity or receiving area for x-ray imaging plate
600 Computer processing system
601 Communications bus
605 Imaging plate
610 Wireless communications system for computer processing system
615 Imaging plate identification device
620 Identification device reader system
630 Internal user interface device
640 Removable media reader device
645 Digital audio recording device
650 Microcontroller computer
651 Microprocessor digital input/output (I/O) port
660 X-Ray beam detection device
661 Threshold detection circuit to determine X-Ray beam duration
670 Orientation (to gravity) detection sensor system
680 Power Supply/Battery
681 Serial interface to batteries state of charge monitoring integrated circuit
685 Power supply capacity determination device
690 External power supply

What is claimed is:

1. An electronic apparatus for capturing information associated with an x-ray image recordable on an x-ray imaging plate, the apparatus comprising:

a housing configured to be held in a hand of a user of the apparatus;

a receiving area formed in the housing, for selectively and individually receiving either a first x-ray imaging plate comprising a computed radiography cassette or a second x-ray imaging plate comprising a digital radiography image receptor, the receiving area retaining a received x-ray imaging plate in a position for image capture during patient exposure;

a display disposed in the housing;

a power supply disposed in the housing for powering the display;

one or more non-image sensors disposed in the housing adapted to collect non-image information associated with the x-ray image recorded on the x-ray imaging plate received in the receiving area; and a computer system disposed in the housing, the computer system including memory adapted to receive, measure, store, and subsequently communicate to another computer system, the collected information from the non-image sensors and associated with the x-ray image recorded on the x-ray imaging plate.

2. The apparatus of claim 1, wherein the receiving area is configured to receive a scatter reducing grid.

3. The apparatus of claim 2, wherein the one or more non-image sensors detect if a scatter reducing grid is received in the receiving area, and the collected information comprises the presence or absence of the grid.

4. The apparatus of claim 2, wherein the one or more non-image sensors identifies an identifier of a particular scatter reducing grid, and the identifier is associated with a physical property of the scatter reducing grid, and wherein the collected information comprises the identifier for the particular scatter reducing grid.

5. The apparatus of claim 1, further including a bar-code scanning device configured to read and record a bar code label affixed to the imaging plate.

6. The apparatus of claim 1, further including a sensor to read and record an RFID label affixed to the imaging plate.

7. The apparatus of claim 1, wherein the one or more non-image sensors includes at least one sensor to measure and record the degree of tilt of the apparatus relative to the direction of gravity in one or more directions.

8. The apparatus of claim 1, further including a radio-receiver to receive and record information from one or more external sensors that are not permanently physically attached to the apparatus.

9. The apparatus of claim 8, wherein the radio-receiver communicates with a distance measuring device that is not permanently physically attached to the apparatus, and records one or more distance measurements made by the distance measuring device in association with the acquisition of a radiographic image.

10. The apparatus of claim 1, further including a removable digital storage media that can be detached and subsequently attached to a reader device and in electronic communication with the computer system to communicate information recorded by the apparatus.

11. The apparatus of claim 1, further including a radio frequency transmitter to communicate information recorded by the apparatus to an external computer system.

12. The apparatus of claim 1, further including an infrared transmitter to communicate information recorded by the apparatus to an external computer system.

13. The apparatus of claim 1, further including a database of medical image examinations, means to display records from the database on the display, and means to select the displayed records and associate the selected records with an image recorded by the imaging plate.

14. The apparatus of claim 1, further including a sensor and a means to record the exact or approximate time the imaging plate recorded an image.

15. The apparatus of claim 1, wherein the one or more non-image sensors collect information associated with at least one of the following: the detection of an x-ray beam; distance sensing; measurement of source-to-patient distance; presence or absence of a grid; grid identification; imaging plate orientation; time of exposure; and exposure duration.

16. A hand-held electronic apparatus for capturing information associated with an x-ray image recordable on an x-ray imaging plate, comprising:
 a housing adapted for holding by a hand of a user of the apparatus;
 a receiving area formed in the housing and adapted to selectively and independently receive either a first x-ray imaging plate comprising a computed radiography cassette or a second x-ray imaging plate comprising a digital radiography image receptor, the receiving area retaining a received x-ray imaging plate in a position for image capture during patient exposure;
 an electronic display disposed on the housing and viewable by the user;
 one or more sensors on the housing adapted to collect non-image information associated with the x-ray image; and
 a computer system disposed on the housing including memory adapted to store both non-sensor information received from a device in electronic communication with the apparatus and the non-image information received from the one or more sensors.

17. The apparatus of claim 16, further comprising means for transmitting, editing, displaying, or storing at least one of the non-sensor information and the non-image information.

18. The apparatus of claim 16, wherein the non-sensor information includes at least one of the following: a work list, exposure information, patient information, technician information, requesting physician information, and work request information.

19. The apparatus of claim 16, wherein the non-image information includes at least one of the following: x-ray beam detection; distance information; measurement of source-to-patient distance; presence or absence of a grid; grid identification; imaging plate orientation; apparatus orientation; exposure time; and exposure duration.

20. The apparatus of claim 16, further comprising digital audio means for collecting audio information.

21. An electronic apparatus for capturing information associated with an x-ray image, comprising:
 a holder, configured to be held in a hand of a user of the apparatus, supporting and operably receiving an x-ray imaging plate that records the x-ray image, the holder adapted for positioning the x-ray imaging plate on a side of a patient opposite an x-ray source with the x-ray imaging plate in position for image acquisition;
 a display disposed on the holder;
 one or more sensors disposed on the holder for collecting non-image information associated with the x-ray image recorded on the imaging plate; and
 a memory disposed on the holder in communication with the one or more sensors to receive and store the non-image information for subsequent transfer to a remote computer system.

* * * * *